(12) United States Patent
Majima et al.

(10) Patent No.: US 6,198,797 B1
(45) Date of Patent: Mar. 6, 2001

(54) X-RAY CT APPARATUS AND IMAGE DIAGNOSTIC APPARATUS

(75) Inventors: Kaoru Majima; Shoko Sato; Shogo Azemoto, all of Tokyo; Manabu Minami, Kanagawa, all of (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/346,811

(22) Filed: Jul. 2, 1999

(30) Foreign Application Priority Data

Jul. 23, 1998 (JP) .................................................. 10-207362
May 11, 1999 (JP) .................................................. 11-129809

(51) Int. Cl.⁷ .............................. H05G 1/64; A61B 6/03
(52) U.S. Cl. .................................. 378/98; 378/4; 378/901
(58) Field of Search .............................. 378/4, 8, 15, 98, 378/98.2, 94

(56) References Cited

U.S. PATENT DOCUMENTS 5,878,156 * 3/1999 Okumura .............................. 382/118
6,009,186 * 12/1999 Gorrette et al. ..................... 382/110
6,104,827 * 8/2000 Benn et al. .......................... 382/110

\* cited by examiner

Primary Examiner—David V. Bruce
(74) Attorney, Agent, or Firm—Moonray Kojima

(57) ABSTRACT

In order to perform diagnosis of corpulence of the internal organs in a practical level, there is provided an X-ray CT apparatus in which, after an operator specifies a minimum CT value and a maximum CT value for a fat portion and specifies one point in a subcutaneous fat region, subcutaneous fat pixels and visceral fat pixels are automatically retrieved, the area ratio thereof is automatically calculated, histograms of CT values of the subcutaneous fat pixels and the visceral fat pixels are automatically generated, and then fat region images Gs and Gv, the area ratio, and the histograms Hs and Hv are displayed on the same screen.

4 Claims, 8 Drawing Sheets

FIG.4

☐ Whole                 ☐ Whole              Select ?

☒ Subcutaneous          ☐ Subcutaneous

☐ Visceral              ☒ Visceral

|                                  | Whole | Subcutaneous | Visceral |
|---|---|---|---|
| V / S    :       %    Area :     | cm²   | cm²          | cm²      |
| S / W    :       %    Mean :     |       |              |          |
| V / W    :       %    Min  :     |       |              |          |
| Circ1    :       cm   Max  :     |       |              |          |
| Circ2    :       cm   SD   :     |       |              |          |
| Threshold : -150, -50            |       |              |          | image diagnostic apparatus

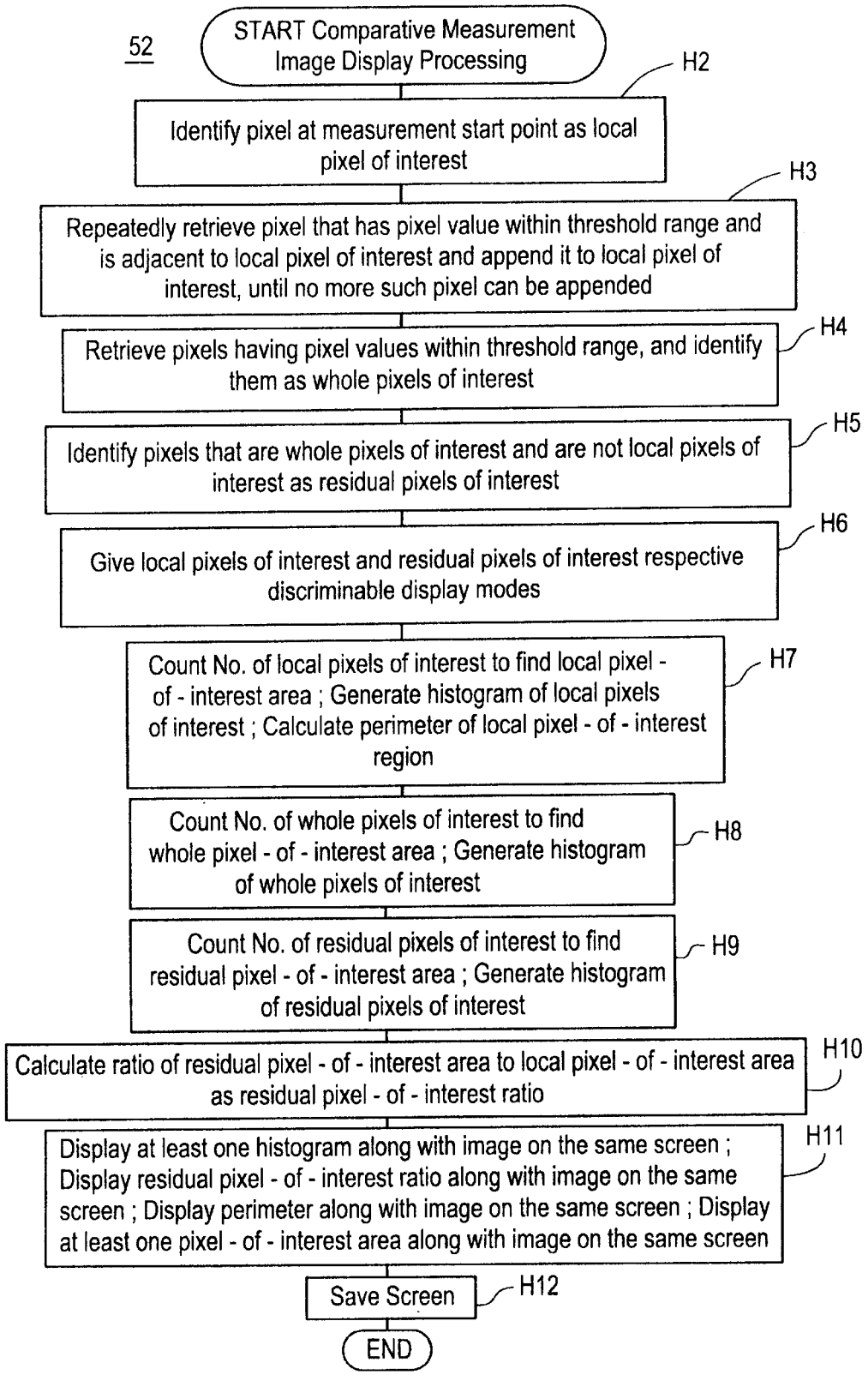

X-RAY CT APPARATUS AND IMAGE DIAGNOSTIC APPARATUS

BACKGROUND OF THE INVENTION

The present invention relates to an X-ray CT (computed tomography) apparatus and an image diagnostic apparatus, and more particularly to an X-ray CT apparatus and an image diagnostic apparatus which enable diagnosis of corpulence of the internal organs in a practical level and are useful for diagnosis of corpulence of the internal organs.

Conventional X-ray CT apparatuses have the following functions:

(1) Density Contour: a function of extracting a region which is composed of continuous pixels having CT values within a threshold range specified by a human operator and contains a measurement start point specified by the operator, and displaying the region in a discriminable mode;

(2) Density Mask: a function of extracting pixels having CT values within a threshold range specified by an operator, and displaying them in a discriminable mode; and (3) Histogram: a function of calculating a histogram of CT values.

By sequentially applying the above-listed functions, the conventional X-ray CT apparatuses may serve to diagnose corpulence of the internal organs.

However, such apparatuses involve inconvenience that they do not provide simultaneous display of the respective screens for these functions, and visceral fat must be manually calculated, causing difficulty in the diagnosis of corpulence of the internal organs in a practical level.

SUMMARY OF THE INVENTION

It is an object of the present invention to provide an X-ray CT (computed tomography) apparatus and an image diagnostic apparatus which enable diagnosis of corpulence of the internal organs in a practical level and are useful for diagnosis of corpulence of the internal organs.

In accordance with a first aspect of the invention, there is provided an X-ray CT apparatus for successively acquiring data at different view angles while rotating an X-ray tube (or an X-ray tube and a detector) around a subject, and producing a tomographic image for display by means of a reconstruction operation (or interpolation and reconstruction operations), comprising: threshold range defining means for specifying CT values for a fat portion in the tomographic image to define a threshold range; measurement start point specifying means for specifying one point in a subcutaneous fat region on the image; subcutaneous fat pixel retrieving means for retrieving pixels within a region on the tomographic image that is composed of continuous pixels having CT values within the threshold range and contains the measurement start point, and identifying these pixels as subcutaneous fat pixels; visceral fat pixel retrieving means for retrieving pixels on the tomographic image that have CT values within the threshold range and are not the subcutaneous fat pixels, and identifying these pixels as visceral fat pixels; fat region image display means for displaying at least either of the subcutaneous fat pixels or the visceral fat pixels in a discriminable mode; area ratio calculating means for calculating the ratio of the area of the subcutaneous fat pixels and the area of the visceral fat pixels; histogram generating means for generating at least one of a histogram of the pixel values of the subcutaneous fat pixels and a histogram of the pixel values of the visceral fat pixels; and composite screen display means for displaying the area ratio and the histograms along with the fat region image on the same screen.

According to the X-ray CT apparatus of the first aspect, the operator is only required to specify minimum and maximum CT values for the fat portion or specify a central CT value and a CT value width for the fat portion, and specify one point in the subcutaneous fat region on the screen. Then the subcutaneous fat pixels and the visceral fat pixels are automatically retrieved, the area ratio thereof is automatically calculated, and the histograms of their pixel values are automatically generated. Next, the fat region image, the area ratio and the histograms are displayed on the same screen. Thus, the diagnosis of corpulence of the internal organs is facilitated.

In accordance with a second aspect of the invention, there is provided the X-ray CT apparatus as described regarding the first aspect, comprising: fat pixel extracted image display means for displaying a fat pixel extracted image which enables discrimination between pixels having CT values within the threshold range and other pixels; separation line input means for allowing an operator to input a separation line in the image; region separation means for identifying continuous pixels having CT values within the threshold range and lying across the separation line as discontinuous.

For some subjects or under some conditions, the subcutaneous fat region and the visceral fat region may be apparently continuous on a tomographic image. In this case, statistical calculations such as those for finding the area ratio of the subcutaneous fat region and the visceral fat region cannot be performed.

According to the X-ray CT apparatus of the second aspect, even when the subcutaneous fat region and the visceral fat region are apparently continuous, these regions can be separated by the separation line input by the operator. The calculations such as those for finding the area ratio of the subcutaneous fat region and the visceral fat region are thus enabled.

In accordance with a third aspect of the invention, there is provided an image diagnostic apparatus for displaying an image and extracting features of a region of interest in the image, comprising: threshold range defining means for specifying pixel values of pixels of interest in the image to define a threshold range; measurement start point specifying means for specifying one point in a local region on the image; local pixel-of-interest retrieving means for retrieving pixels within a region on the image that is composed of continuous pixels having pixel values within the threshold range and contains the measurement start point, and identifying these pixels as local pixels of interest; residual pixel-of-interest retrieving means for retrieving pixels on the image that have pixel values within the threshold range and are not the local pixels of interest, and identifying these pixels as residual pixels of interest; pixel-of-interest region image display means for displaying at least either of the local pixels of interest or the residual pixels of interest in a discriminable mode; area ratio calculating means for calculating the ratio of the area of the local pixels of interest and the area of the residual pixels of interest; histogram generating means for generating at least one of a histogram of the pixel values of the local pixels of interest and a histogram of the pixel values of the residual pixels of interest; and composite screen display means for displaying the area ratio and the histograms along with the pixel-of-interest region image on the same screen.

According to the image diagnostic apparatus of the third aspect, the operator is only required to specify minimum and maximum pixel values for the pixels of interest or specify a central pixel value and a pixel value width for the pixels of interest, and specify one point in the local region on the screen. Then the local pixels of interest and the residual pixels of interest are automatically retrieved, the area ratio thereof is automatically calculated and the histograms of their pixel values are automatically generated. Next, the pixel-of-interest region image, the area ratio and the histograms are displayed on the same screen. Thus, the features of the pixels of interest can be easily observed. For example, diagnosis of corpulence of the internal organs is facilitated.

In accordance with a fourth aspect of the invention, there is provided the image diagnostic apparatus as described regarding the third aspect, comprising: pixel-of-interest extracted image display means for displaying a pixel-of-interest extracted image which enables discrimination between pixels having pixel values within the threshold range and other pixels; separation line input means for allowing an operator to input a separation line in the image; region separation means for identifying continuous pixels having pixel values within the threshold range and lying across the separation line as discontinuous.

For some subjects or under some conditions, the local pixel-of-interest region and the residual pixel-of-interest region may be apparently continuous on a tomographic image. In this case, statistical calculations such as those for finding the area ratio of the local pixel-of-interest region and the residual pixel-of-interest region cannot be performed.

According to the image diagnostic apparatus of the fourth aspect, even when the local pixel-of-interest region and the residual pixel-of-interest region are apparently continuous, these regions can be separated by the separation line input by the operator. The calculations such as those for finding the area ratio of the local pixel-of-interest region and the residual pixel-of-interest region are thus enabled.

As described above, the X-ray CT apparatus and the image diagnostic apparatus of the present invention have the following advantages.

According to the X-ray CT apparatus of the present invention, only by specifying a threshold range to define a fat portion and specifying one point in a subcutaneous fat region, an image which enables discrimination of the fat portion is displayed and the visceral fat ratio and histograms are displayed on the same screen. Therefore, diagnosis and examination of corpulence of the internal organs caused by adult-onset diseases can easily be done. Moreover, since the regions can be arbitrarily separated, even when the subcutaneous fat region and the visceral fat region are (apparently) continuous these region can be separated, enabling statistical calculations such as those for finding the area ratio.

According to the image diagnostic apparatus of the present invention, only by specifying a threshold range to define pixels of interest and specifying one point in a local region, an image which enables discrimination of the pixel-of-interest region is displayed and the area ratio and histograms are displayed on the same screen. Therefore, the features of the pixels of interest can be intuitively recognized. Moreover, since the regions can be arbitrarily separated, even when the local pixel-of-interest region and the residual pixel-of-interest region are (apparently) continuous these region can be separated, enabling statistical calculations such as those for finding the area ratio.

Further objects and advantages of the present invention will be apparent from the following description of the preferred embodiments of the invention as illustrated in the accompanying drawings.

BRIEF DESCRIPTION OF THE DRAWINGS

FIG. 4 an exemplary illustration of a screen for selecting a screen layout.

FIG. 10 is a flow chart of comparative measurement image display processing conducted by the image diagnostic apparatus of FIG. 8.

DETAILED DESCRIPTION OF THE INVENTION

The present invention will now be described in more detail with reference to embodiments shown in the accompanying drawings.

First Embodiment

Figure 1:
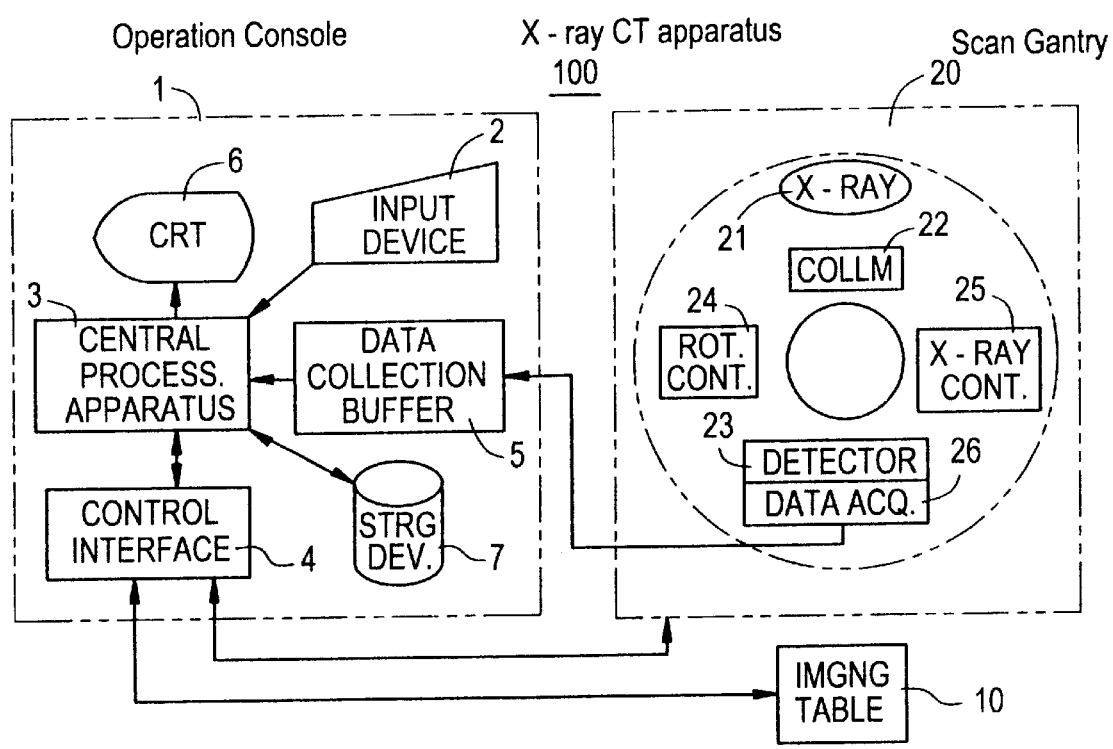
FIG. 1 is a configuration diagram illustrating an X-ray CT apparatus in accordance with a first embodiment of the present invention.

FIG. 1 is a configuration diagram of an X-ray CT apparatus in accordance with a first embodiment of the invention.

The X-ray apparatus 100 comprises an operation console 1, an imaging table 10 and a scan gantry 20.

The operation console 1 comprises an input device 2 for accepting commands and parameters input by a human operator, a central processing apparatus 3 for conducting scan processing, image reconstruction processing, fat measurement parameter specifying processing, fat measurement image display processing and the like, a control interface 4 for supplying control signals etc. to the imaging table 10 and the scan gantry 20, a data collection buffer 5 for collecting data obtained from the scan gantry 20, a CRT 6 for displaying images etc., and a storage device 7 for storing several data and programs.

The imaging table 10 moves a subject rested thereon in the direction of the subject's body axis.

The scan gantry 20 comprises an X-ray tube 21, a collimator 22, a detector 23, a rotation controller 24 for rotating the X-ray tube 21 and the detector 23 etc. around the subject's body axis, an X-ray controller 25 for regulating the timing and strength of X-ray emission, and a data acquisition section 26.

Figure 2:
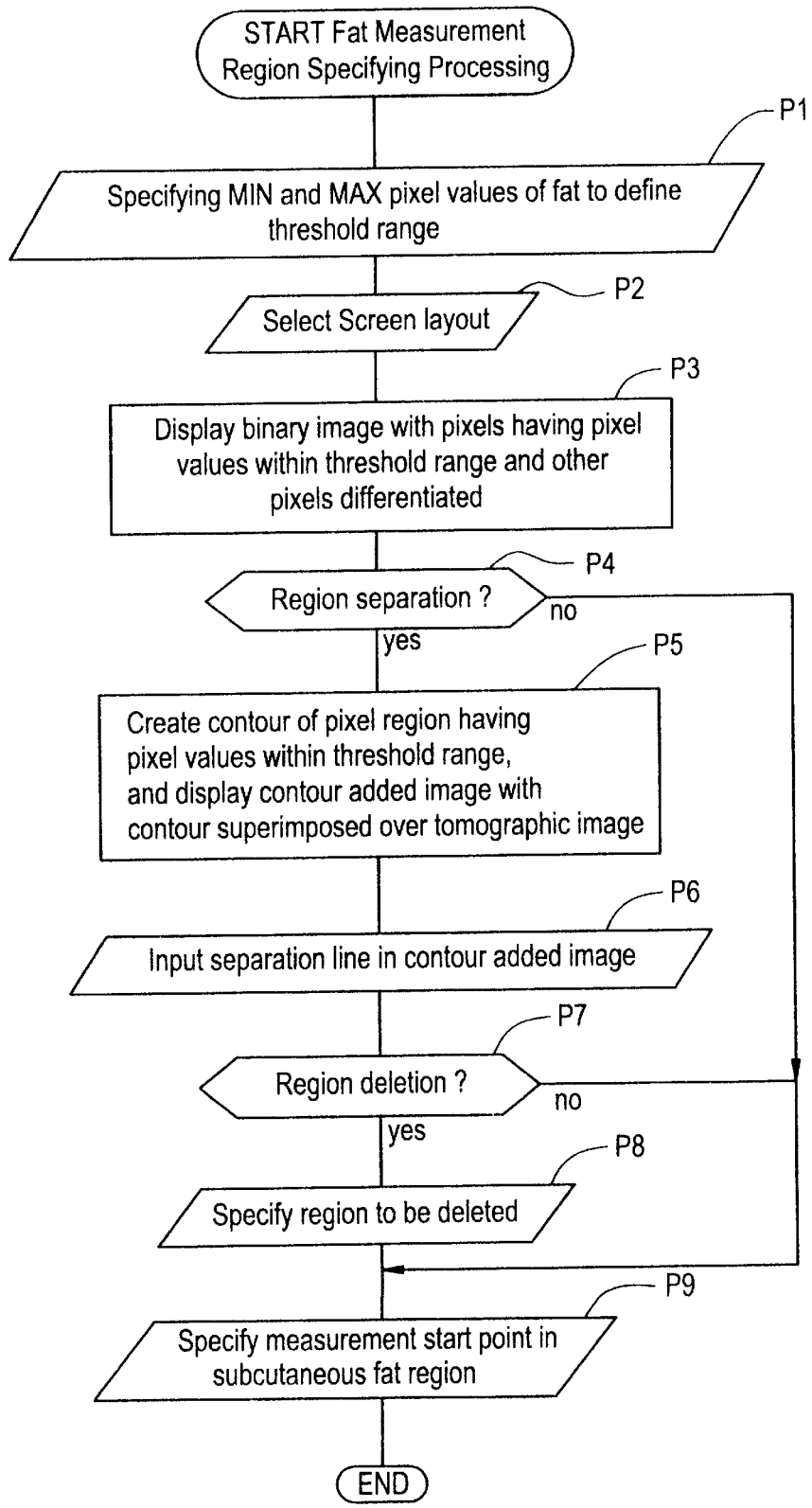
FIG. 2 is a flow chart of fat measurement region specifying processing conducted by the X-ray CT apparatus of FIG. 1.

FIG. 2 is a flow chart of fat measurement region specifying processing conducted by the X-ray CT apparatus 100.

In Step P1, a minimum CT value (e.g., −150) and a maximum CT value (e.g., −50) for fat input by the operator are accepted to define a threshold range. Alternatively, a central CT value (e.g., −100) and a CT value width (e.g., 50) for fat input by the operator may be accepted to define the threshold range.

In Step P2, screen layout options are displayed on the screen and allows the operator to make a choice. For example, the operator chooses what to display in areas enclosed by broken line among 'Whole' fat, 'Subcutaneous' fat and 'Visceral' fat, as shown in FIG. 4. In this example, the subcutaneous fat is chosen for the left area, and the visceral fat is chosen for the right area.

In Step P3, a binary image is created for display in which the pixel value for pixels having CT values within the threshold range on the tomographic image is one, and the pixel value for other pixels is zero. Alternatively, a color image may be displayed instead of the binary image in which the pixels having CT values within the threshold range are displayed in a specific color.

Figure 5A:
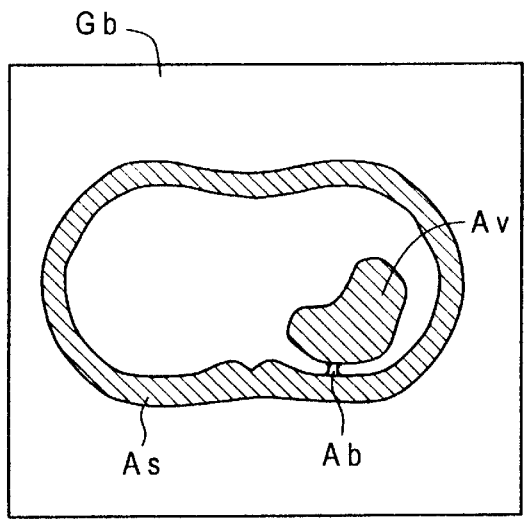
FIG. 5 is a schematic representation of a binary image in which a fat region is extracted and a contour added image in which the contour of the fat region is added to a tomographic image.

FIG. 5(a) exemplarily shows the binary image Gb. In the binary image Gb, the subcutaneous fat region As and the visceral fat region Av are shown as apparently continuous connected via a bridge portion Ab.

In Step P4, the operator decides whether to conduct region separation. If the region separation is selected, the process goes to Step P5, otherwise to Step P9.

Figure 5B:
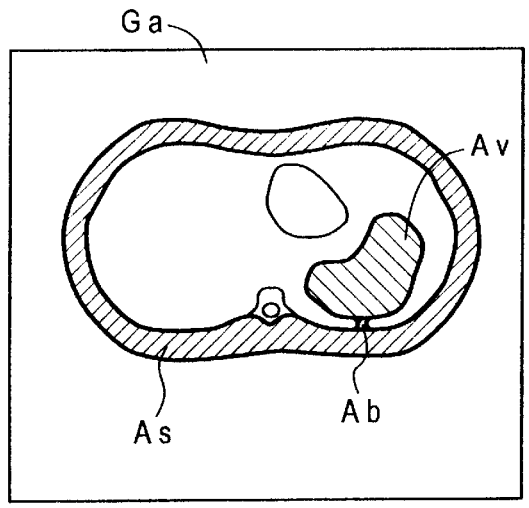

In Step P5, a contour is extracted of the region having a pixel value of one in the binary image Gb, and, as shown in FIG. 5(b), a contour added image Ga is displayed with the contour superimposed over the tomographic image.

Figure 6:
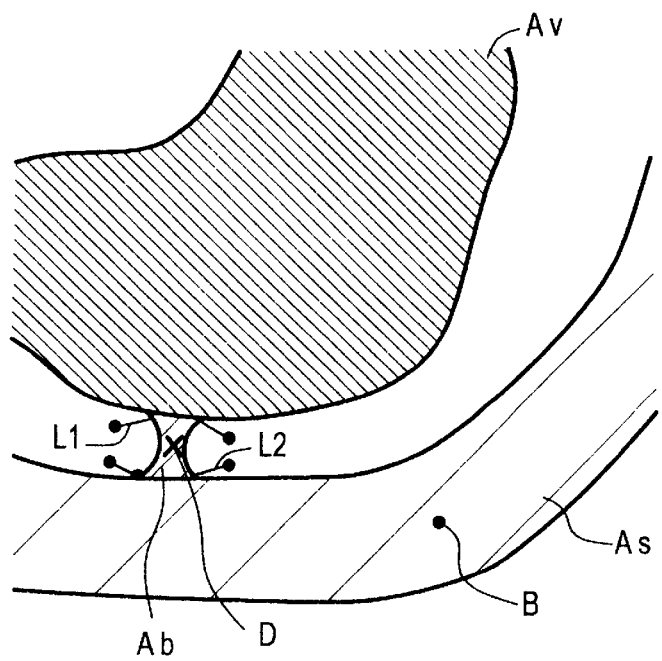
FIG. 6 a explanatory diagram illustrating input of separation lines and a measurement start point.

In Step P6, the operator inputs separation lines L1 and L2 on the contour added image Ga, as shown in FIG. 6. The process of inputting the separation line is achieved by successively inputting points using, for example, a trackball and a return key to cause the points to sequentially connected by straight lines, and pushing the return key twice at the last point. Alternatively, the points may be successively input by clicking a mouse to cause the points to be sequentially connected by straight lines, and double-clicking the mouse at the last point. Either one, two or more separation lines may be input as needed. After the separation lines has been input, the pixel values for the pixels in the original binary image Gb on the separation lines are changed into zero.

In Step P7, the operator decides whether to conduct region deletion. When the region deletion is selected, the process goes to Step P8, otherwise to Step P9.

In Step P8, the operator specifies a region to be deleted on the contour added image Ga. For example, a region interposed between the separation lines L1 and L2 is specified in FIG. 6. Upon specifying the region, a mark D indicative of deletion is displayed in the specified region. At the same time, the pixel values for the pixels in the original binary image Gb within the specified region is changed into zero.

In Step P9, the operator specifies a measurement start point B in the visceral fat region As on the contour added image Ga, as shown in FIG. 6. Then the fat measurement region specifying process is terminated.

Figure 3:
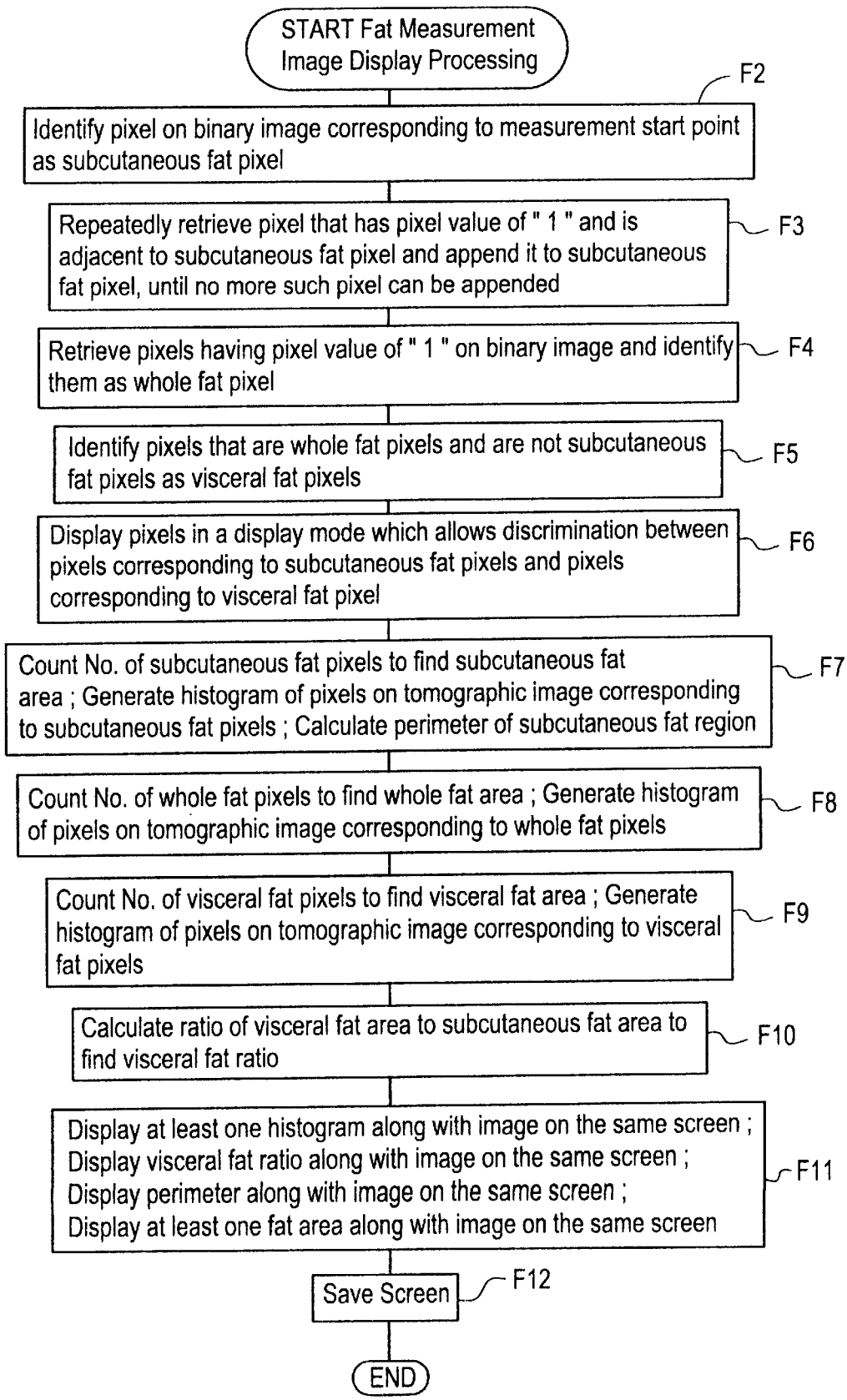
FIG. 3 is a flow chart of fat measurement image display processing conducted by the X-ray CT apparatus of FIG. 1.

FIG. 3 is a flow chart of fat measurement image display processing by the X-ray CT apparatus 100.

In Step F2, a pixel on the binary image Gb corresponding to the measurement start point B is identified as a subcutaneous fat pixel.

In Step F3, a pixel that has a pixel value of one and is adjacent to the subcutaneous fat pixel is retrieved and appended to the subcutaneous fat pixel; and this step is repeated. When no more pixel to be appended is found, the process goes to Step F4.

In Step F4, pixels having a pixel value of one are retrieved on the binary image Gb and identified as whole fat pixels.

In Step F5, pixels in the binary image Gb that are the whole fat pixels and are not the subcutaneous fat are identified as visceral fat pixels.

In Step F6, the tomographic images are displayed in a display mode which allows discrimination between the pixels corresponding to the subcutaneous fat pixels and the pixels corresponding to the visceral fat pixels, as shown in FIG. 5, according to the aforementioned screen layout selection, in which, in this example, the subcutaneous fat region image and the visceral fat region image have been selected for display. (In FIG. 5, the regions are shown as different patterns of hatching.)

In Step F7, the number of subcutaneous fat pixels is counted and the number is identified as a subcutaneous fat area. Moreover, a histogram of the CT values of the pixels on the tomographic image corresponding to the subcutaneous fat pixels is generated. Furthermore, the perimeter of the subcutaneous fat pixel region is calculated.

In Step F8, the number of whole fat pixels is counted and the number is identified as a whole fat area. Moreover, a histogram of the CT values of the pixels on the tomographic image corresponding to the whole fat pixels is generated.

In Step F9, the number of visceral fat pixels is counted and the number is identified as a visceral fat area. Moreover, a histogram of the CT values of the pixels on the tomographic image corresponding to the visceral fat pixels is generated.

In Step F10, the ratio of the visceral fat area to the subcutaneous fat area is calculated and the ratio is identified as a visceral fat ratio.

Figure 7:
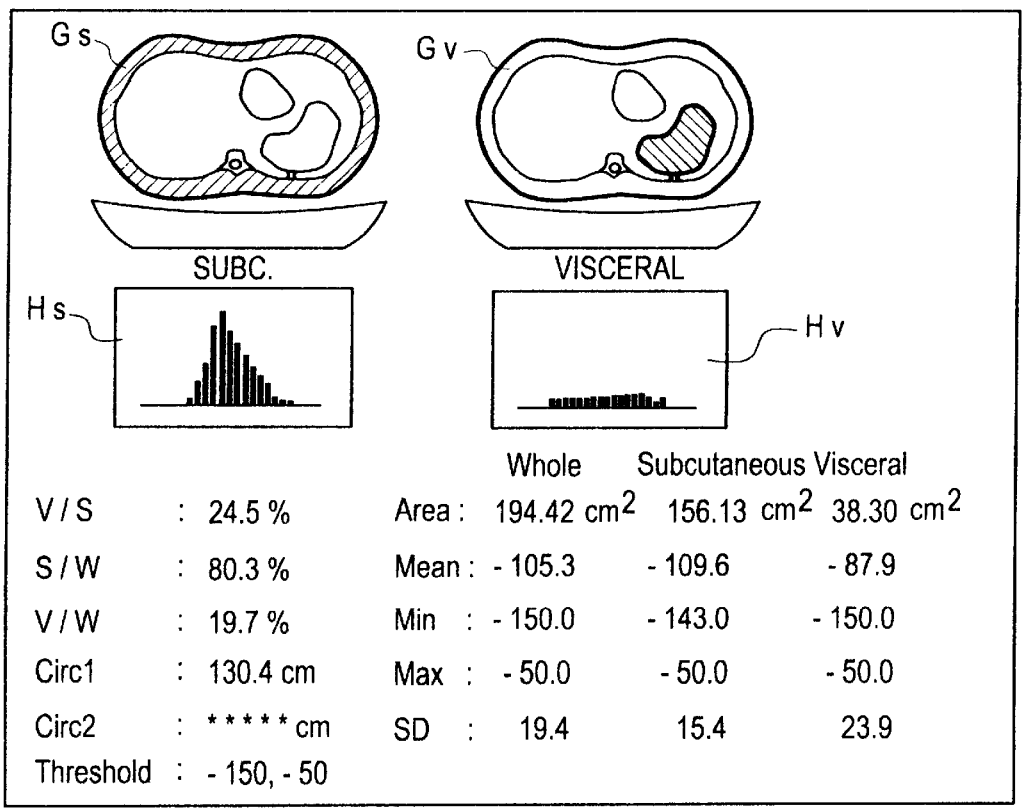
FIG. 7 is an exemplary illustration of a screen layout for displaying an axial image of the abdomen in which the fat portion is displayed in a discriminable mode and histograms on the same screen.

In Step F11, the subcutaneous fat region image Gs and the histogram Hs of the CT values of the subcutaneous fat pixels are displayed on the left side, and the visceral fat region image Gv and the histogram Hv of the CT values of the visceral fat pixels are displayed on the right side on the same screen, as shown in FIG. 7, according to the screen layout selection, in which, in this example, the subcutaneous fat and the visceral fat have been selected for the left and right areas, respectively. Additionally, on the same screen are displayed the visceral fat ratio (V/S=visceral fat area÷subcutaneous fat area×100), the subcutaneous fat proportion (S/W=subcutaneous fat area÷whole fat area×100), the visceral fat proportion (V/W=visceral fat area÷whole fat area×100), the subcutaneous fat region perimeter (Circ1), the perimeter of an arbitrarily specified region (Circ2), the respective areas (Area), mean CT values (Mean), actual minimum CT values (Min), actual maximum CT values (Max) and standard deviations (Sd) of the whole fat, subcutaneous fat and visceral fat.

In Step F12, the screen is saved.

According to the X-ray CT apparatus 100 as described above, the operator is only required to define a CT value range of the fat region and specify one point in the subcutaneous fat region, and the images which allow discrimination between subcutaneous fat and visceral fat are displayed and also the visceral fat ratio and histograms are displayed on the same screen. Thus, the diagnosis of corpulence of the internal organs is facilitated when an axial image of the abdomen is employed as the tomographic image Gf.

Moreover, according to the X-ray CT apparatus 100, even when the subcutaneous fat region and the visceral fat region are (apparently) continuous, these regions can be separated by the separation line input by the operator, thereby enabling the area ratio etc. to be calculated.

Second Embodiment

Figure 8:
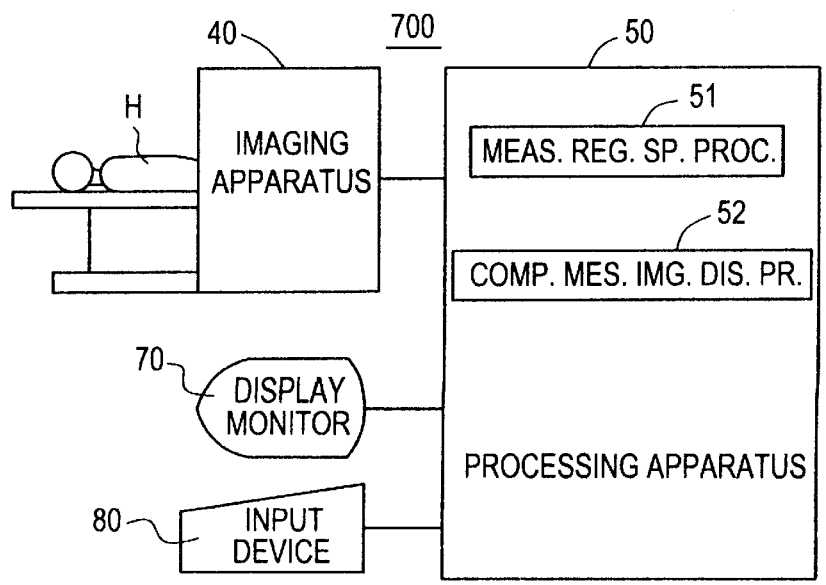
FIG. 8 is a configuration diagram of an image diagnostic apparatus in accordance with a second embodiment of the present invention.

FIG. 8 is a configuration diagram of an image diagnostic apparatus in accordance with a second embodiment of the present invention.

The image diagnostic apparatus 700 comprises an imaging apparatus 40 for imaging a subject H such as an X-ray CT apparatus, MRI (magnetic resonance imaging) apparatus and ultrasonic diagnostic apparatus, a processing apparatus 50 for performing measurement parameter specifying processing 51 and comparative measurement image display processing 52 in accordance with the present invention on an image obtained by the imaging apparatus 40, a display monitor 70, and an input device 80.

Figure 9:
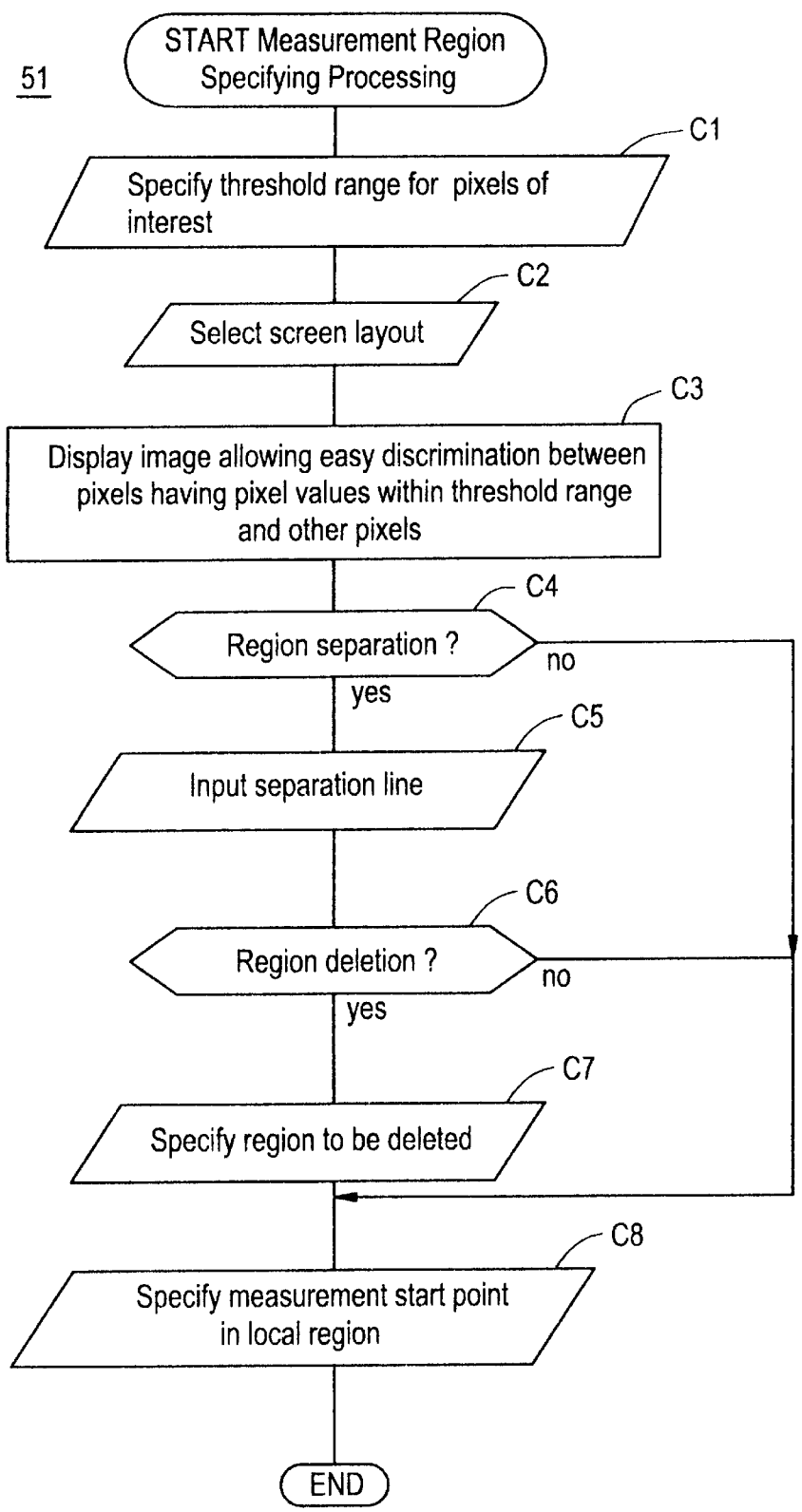
FIG. 9 is a flow chart of measurement region specifying processing conducted by the image diagnostic apparatus of FIG. 8.

FIG. 9 is a flow chart of the measurement region specifying processing 51 by the image diagnostic apparatus 700.

In Step C1, minimum and maximum pixel values (e.g., CT value or brightness value) of pixels of interest input by a human operator are accepted to define a threshold range.

In Step C2, a plurality of screen layout patterns are displayed on the screen to allow the operator to make a choice.

In Step C3, an image which allows easy discrimination between pixels having pixel values within the threshold range and other pixels is produced for display.

In Step C4, the operator decides whether to conduct region separation. If the region separation is selected, the process goes to Step C5, otherwise to Step C8.

In Step C5, the operator inputs a separation line on the image. After the separation line has been input, the continuous pixels having pixel values within the threshold range and lying across the separation line are regarded as discontinuous.

In Step C6, the operator decides whether to conduct region deletion. If the region deletion is selected, the process goes to Step C7, otherwise to Step C8.

In Step C7, the operator specifies a region to be deleted on the image. Upon specifying the region, the pixel values in the specified region are regarded as having pixel values out of the threshold range.

In Step C8, the operator specifies a measurement start point in a local region on the image. Then the measurement region specifying processing is terminated.

FIG. 10 is a flow chart of the comparative measurement image display processing 52 by the image diagnostic apparatus 700.

In Step H2, a pixel at the measurement start point is identified as a local pixel of interest on the original image.

In Step H3, a pixel that has a pixel value within the threshold range and is adjacent to the local pixel of interest is retrieved on the original image and appended to the local pixel of interest; and this step is repeated. When no more pixel to be appended to the local pixel of interest is found, the process goes to Step H4.

In Step H4, pixels having pixel values within the threshold range are retrieved on the original image and identified as whole pixels of interest.

In Step H5, pixels that are the whole pixels of interest and are not the local pixels of interest are identified as residual pixels of interest.

In Step H6, if a local pixel-of-interest region image and a residual pixel-of-interest region image are selected for display in the screen layout choice, the local pixels of interest and the residual pixels of interest are given respective discriminable modes.

In Step H7, the number of local pixels of interest is counted and the number is identified as a local pixel-of-interest area. Moreover, a histogram of the pixel values of the local pixels of interest is generated. Furthermore, the perimeter of the local pixel-of-interest region is calculated.

In Step H8, the number of whole pixels of interest is counted and the number is identified as a whole pixel-of-interest area. Moreover, a histogram of the pixel values of the whole pixels of interest is generated.

In Step H9, the number of residual pixels of interest is counted and the number is identified as a residual pixel-of-interest area. Moreover, a histogram of the pixel values of the residual pixels of interest is generated.

In Step H10, the ratio of the residual pixel-of-interest area to the local pixel-of-interest area is calculated and identified as a residual pixel-of-interest ratio.

In Step H11, if the histogram of the pixel values of the local pixels of interest and the histogram of the pixel values of the residual pixels of interest are selected for display in the screen layout choice, the histogram of the pixel values of the local pixels of interest and the histogram of the pixel values of the residual pixels of interest are displayed along with the local pixel-of-interest region image and the residual pixel-of-interest region image on the same screen. Moreover, the residual pixel-of-interest ratio, the perimeter, the local pixel-of-interest area and the residual pixel-of-interest area are displayed on the same screen.

In Step H12, the screen is saved.

According to the image diagnostic apparatus 700 as described above, the operator is only required to define a pixel value range of the pixels of interest and specify one point in the local region, and the local pixels of interest and the residual pixels of interest are displayed on an image in a discriminable mode and also the area ratio and histograms are displayed on the same screen. Thus, the features of the pixels of interest can be easily observed.

Moreover, according to the image diagnostic apparatus 700, even when the local pixel-of-interest region and the residual pixel-of-interest region are (apparently) continuous, these regions can be separated, thereby enabling the area ratio etc. to be calculated.

If an axial image of the abdomen is employed as the original image with fat pixels selected as the pixels of interest and a subcutaneous fat region selected as the local region, then diagnosis of corpulence of the internal organs can be performed. Moreover, diagnosis of a lesion site in the liver or in the brain can be performed.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus for acquiring data while rotating an X-ray tube around a subject, and producing a tomographic image for display by means of a reconstruction operation, comprising:

threshold range defining means for specifying CT values for a fat portion in said tomographic image to define a threshold range;

measurement start point specifying means for specifying one point in a subcutaneous fat region on the image;

subcutaneous fat pixel retrieving means for retrieving pixels within a region on said tomographic image that is composed of continuous pixels having CT values within said threshold range and contains said measurement start point, and identifying these pixels as subcutaneous fat pixels;

visceral fat pixel retrieving means for retrieving pixels on said tomographic image that have CT values within said threshold range and are not the subcutaneous fat pixels, and identifying these pixels as visceral fat pixels;

fat region image display means for displaying at least either of the subcutaneous fat pixels or the visceral fat pixels in a discriminable mode;

area ratio calculating means for calculating the ratio of the area of said subcutaneous fat pixels and the area of said visceral fat pixels;

histogram generating means for generating at least one of a histogram of the CT values of said subcutaneous fat pixels and a histogram of the CT values of said visceral fat pixels; and composite screen display means for displaying said area ratio and said histograms along with said fat region image on the same screen.

2. The X-ray CT apparatus as defined by claim 1, comprising:

fat pixel extracted image display means for displaying a fat pixel extracted image which enables discrimination between pixels having CT values within said threshold range and other pixels;

separation line input means for allowing an operator to input a separation line in the image;

region separation means for identifying continuous pixels having CT values within said threshold range and lying across said separation line as discontinuous.

3. An image diagnostic apparatus for displaying an image and extracting features of pixels of interest in said image, comprising:

threshold range defining means for specifying pixel values of pixels of interest in said image to define a threshold range;

measurement start point specifying means for specifying one point in a local region on the image;

local pixel-of-interest retrieving means for retrieving pixels within a region on said image that is composed of continuous pixels having pixel values within said threshold range and contains said measurement start point, and identifying these pixels as local pixels of interest;

residual pixel-of-interest retrieving means for retrieving pixels on said image which have pixel values within said threshold range and are not the local pixels of interest, and identifying these pixels as residual pixels of interest;

pixel-of-interest region image display means for displaying at least either of the local pixels of interest or the residual pixels of interest in a discriminable mode;

area ratio calculating means for calculating the ratio of the area of said local pixels of interest and the area of said residual pixels of interest;

histogram generating means for generating at least one of a histogram of the pixel values of said local pixels of interest and a histogram of the pixel values of said residual pixels of interest;

composite screen display means for displaying said area ratio and said histograms along with said pixel-of-interest region image on the same screen.

4. The image diagnostic apparatus as defined by claim 3, comprising:

pixel-of-interest extracted image display means for displaying a pixel-of-interest extracted image which enables discrimination between pixels having pixel values within said threshold range and other pixels;

separation line input means for allowing an operator to input a separation line in the image;

region separation means for identifying continuous pixels having pixel values within said threshold range and lying across said separation line as discontinuous.

* * * * *